US 6,634,233 B2

(12) United States Patent
He

(10) Patent No.: US 6,634,233 B2
(45) Date of Patent: Oct. 21, 2003

(54) METHOD FOR DETERMINING THE WALL THICKNESS AND THE SPEED OF SOUND IN A TUBE FROM REFLECTED AND TRANSMITTED ULTRASOUND PULSES

(75) Inventor: Ping He, Centerville, OH (US)

(73) Assignee: Wright State University, Dayton, OH (US)

( * ) Notice: Subject to any disclaimer, the term of this patent is extended or adjusted under 35 U.S.C. 154(b) by 85 days.

(21) Appl. No.: 10/055,461

(22) Filed: Jan. 23, 2002

(65) Prior Publication Data

US 2002/0134159 A1 Sep. 26, 2002

Related U.S. Application Data

(60) Provisional application No. 60/263,650, filed on Jan. 23, 2001.

(51) Int. Cl.$^7$ ............................................... G01N 29/02
(52) U.S. Cl. ............................. 73/597; 73/602; 73/622
(58) Field of Search ..................... 73/597, 622, 602, 73/628; 702/171

(56) References Cited

U.S. PATENT DOCUMENTS

| | | | |
|---|---|---|---|
| 3,930,404 A | | 1/1976 | Ryden, Jr. |
| 4,027,527 A | | 6/1977 | Bennett et al. |
| 4,049,954 A | | 9/1977 | Da Costa Vieira et al. |
| 4,099,418 A | | 7/1978 | Bennett et al. |
| 4,254,660 A | | 3/1981 | Prause |
| 4,404,853 A | | 9/1983 | Livingston |
| 4,475,399 A | | 10/1984 | Livingston |
| 4,487,072 A | | 12/1984 | Livingston |
| 4,740,146 A | | 4/1988 | Angelbeck |
| 5,063,780 A | * | 11/1991 | Landry et al. ................ 73/622 |
| 5,156,636 A | | 10/1992 | Kuljis |
| 5,596,508 A | | 1/1997 | Cuffe |

OTHER PUBLICATIONS

Kuo et al., A novel method for the measurement of acoustic speed. J. Acoust. Soc. Am. 88 (4), Oct. 1990, p. 1679–1682.
Hsu et al., Simultaneous ultrasonic velocity and sample thickness measurement and application in composites, J. Acoust. Soc. Am. 92 (2), Pt. 1, Aug. 1992, p. 669–675.
He, Ping; Simultaneous measurement of sound velocity and wall thickness of a tube; Ultrasonics; 2001; 407–411; 39; Elsevier Science B.V.; United States.
He, Ping; Measurement of acoustic dispersion using both transmitted and reflected pulses; J. Acoust. Soc. Am.; Feb. 2000; 801–807; 107–2; Acoustical Society of America; United States.

* cited by examiner

Primary Examiner—John E. Chapman
(74) Attorney, Agent, or Firm—Killworth, Gottman, Hagan & Schaeff LLP

(57) ABSTRACT

A method for the determining ultrasonic sound propagation speed and wall thickness of a tubular object. Time-domain and frequency-domain analyses are used, where the latter can determine acoustic dispersion if the specimen is made up of a dispersive material. Time of flight data is sensed from a series of transmitted ultrasonic waves, some of which are reflected and some of which are transmitted. The time of flight data can be used to calculate speed of sound in the tube, as well as wall thickness. Inherent in the time of flight data is the speed of the ultrasonic wave; accordingly, correction for temperature variations in the tube is not required. The calculations based on measured speed of sound quantities produces more accurate results than in calculations where the speed of sound in the specimen is assumed.

18 Claims, 5 Drawing Sheets

METHOD FOR DETERMINING THE WALL THICKNESS AND THE SPEED OF SOUND IN A TUBE FROM REFLECTED AND TRANSMITTED ULTRASOUND PULSES

This application claims the benefit of U.S. Provisional Application No. 60/263,650 filed Jan. 23, 2001.

BACKGROUND OF THE INVENTION

The present invention generally relates to the use of ultrasonic pulses, or waves, to measure the properties of objects in the wave's path, and more particularly to the use of an ultrasonic wave source to determine both the thickness of pipes and tubes and the speed of sound within the same, both from the same set of measured time of flight data and without recourse to assumed or predetermined values of properties unique to the pipe or tube being measured.

Various types of non-destructive measurement methods have been employed in the art for determining an object's structural properties. One method, utilizing ultrasonic waves, is particularly appealing due to its accuracy, relative low cost, and safety. It is commonly used to determine object thickness, as well as to detect flaws and discontinuities. Accordingly, its use in inspecting objects with hollow internal cavities not readily amenable to visual perception or the placement of a conventional measuring device is especially valuable. Exploitation of the wavelike nature of acoustically propagated signals, when combined with knowledge of the constitutive properties of the material making up the object, leads to reasonably accurate measurement of the object. Ultrasonic testing is well-suited to the measurement of material thickness, including layered or nonhomogenous materials with acoustically disparate properties. By taking advantage of different reflective properties of the constituent materials and the speed of propagation of the sound wave therethrough, the thickness of the material can be readily calculated.

The operation of a conventional ultrasonic measurement system in the time domain is relatively straightforward. Typically, a pulse generator produces an electrical signal with certain characteristics. This signal is sent to one or more transducers, where the signal is converted to an ultrasonic wave, which is then transmitted in the direction of a target object to be measured. Typically, both the target object as well as the transducers are in an acoustically-coupled medium, such as water, to enhance the detection of the waves over a more rarified medium, such as air. Echoes reflected from the object return to the transducers, which convert the echo into a corresponding electrical signal, which is then routed to a receiver, where the signals can be counted or digitized, analyzed and stored. Analysis of the echo shows that the thickness of the object can be equated to a product of the speed of sound and the propagation time of the ultrasound wave within the object. Once any two of these three values are known, the third can be easily calculated. Nevertheless, the accuracy of some calculations based on time of flight data is subject to limitations. For example, in the conventional analysis discussed above, the speed of sound in the object being measured is assumed. Furthermore, even if the assumed speed was accurate for one temperature, it might not be for another. In addition, in the conventional analysis, the frequency-dependence of the speed of sound is not considered; the spectral content can become significant if the object being measured exhibits dispersive (i.e.: frequency-dependent) properties. These assumptions and simplifications, based on a constant, predetermined value, may introduce errors into subsequent thickness calculations. Moreover, for objects with multiple walls (such as a tube), there are limitations on placement of the ultrasonic transducers, especially where the inside diameter of the tube is small. Existing methods, while appropriate for geometrically simple structures, such as flat plates, are incapable of measuring individual wall thickness of multi-walled objects.

Current methods to measure the wall thickness of tubes and tubular-shaped objects either depend on an assumed sound velocity in the tube, or use a calibration procedure. Both of these approaches have disadvantages. In the former case, inaccuracies can result, either from improper characterization of the constitutive properties of the material in the object, or from inhomogeneities in the material itself, such as due to the presence of cladding, alloying or composite structures. Insofar as the equations used to calculate thickness depend on the speed of sound in the object being measured, any inaccuracies in that assumed quantity will produce errors in thickness calculations. In the latter case, calibration is complicated and unreliable. In addition, it often must be conducted off-line, thereby taking away from precious measurement time.

It is well-known in the art to compensate measurements for variations in the temperature of the acoustic couplant medium (typically water). However, the temperature of the water can be significantly different than the temperature of the object in the water, especially when the object is passing through the water as part of a manufacturing step, such as the extrusion of tubes and related objects. Thus, assigning a temperature value (such as the measured temperature of the water in which the object is placed) to an object being measured may not accurately reflect the true temperature within the object.

The time-domain method provides a single scalar value of the speed of sound. If the sound wave passes through a dispersive medium, its determination will depend on the frequency characteristics of the transducers used in the measurement. However, an inherent part of the time-domain method is that such frequency-dependent values are not made manifest. Thus, in certain circumstances, additional measurement accuracy can be realized by using frequency-domain analysis, which can determine the phase velocity and group velocity at different frequencies. In the present context, the term "speed", although in the strictest sense speed a scalar quantity, is used generally to represent both scalar and vector quantities in either the time-domain or the frequency-domain. Contrarily, the more specific terms "phase velocity" and "group velocity" are both functions of frequency, and their use is restricted to frequency-domain analyses. The frequency-dependent quantities, while usually not as big of a contributor to a thorough and accurate determination of object thickness as the speed of sound in the object, can nonetheless provide additional insight into secondary levels of measurement error, especially when conducted on dispersive materials.

Accordingly, what is needed is a method for measuring object thickness and sound velocity through the object simultaneously, such that neither assumed properties nor the use of complicated procedures is required. What is further needed is a method that eliminates the need for the associated uncertainty of thickness measurements.

BRIEF SUMMARY OF THE INVENTION

These needs are met by the present invention, where a new method for determining the sound propagation velocity and wall thickness of a tubular workpiece is described. As used in the present context, a tubular workpiece need not be cylindrical in cross-section; it could be elliptical or even rectangular. It will be appreciated by those skilled in the art that the present method could also be used on elongate, non-tubular members, such as cylindrical or elliptical solid rods and related structure. Extraction of the sound velocity and tube thickness from the sensed data obviates the need for using a contact-based method for measuring the tube thickness, which can be either inconvenient or inaccurate under certain conditions. It also avoids calculation errors by utilizing actual measured speed of sound in the tubular workpiece, rather than assuming a fixed, predetermined value. It also extends the use of multiple transducers to objects with complex geometries, such as tubes, where access limitations prohibit transducer configurations for single wall measurements to be used. The method is particular useful for real-time measurement of multiple wall thickness when the sound speed of the specimen may change, such as due to a change of temperature. Unlike the prior art, where the speed of sound in the object is assumed and the measured data is corrected post facto to account for temperature variations within an acoustic couplant medium (or some other location in close proximity to the object), the data taken by the method of the present invention inherently includes temperature-related effects, as the speed of sound through the medium is a necessary concomitant of the time of flight measurements. Accordingly, temperature-related errors are minimized or abrogated entirely. In circumstances where acoustic dispersion within the tube material may be significant, this new method can provide further enhanced accuracy by taking into account the spectral content of the propagated wave through the tube walls.

According to an aspect of the present invention, a method of determining the wall thickness of a tubular workpiece and the speed of sound within the workpiece from a single set of measured time of flight data is disclosed. The method comprises the steps of configuring an acoustic couplant medium and defining a transmission path therein, and selectively disposing the tubular workpiece in the medium such that the workpiece is in the transmission path and that each interface between a surface of the workpiece and the medium along the transmission path defines an acoustic discontinuity. By selectively disposing the workpiece in the transmission path, measurements using the ultrasonic waves being transmitted with and without the presence of the workpiece can be compared. Additional steps of the method include transmitting the waves through the transmission path, receiving signals corresponding to the transmitted and reflected waves, measuring time of flight data for each of the received signals, calculating a speed of sound in the workpiece based on the measured time of flight data, and calculating a thickness of each wall of the workpiece based on the measured time of flight data and the calculated speed of sound.

Optionally, the method can include additional steps, such as compensating the speed of sound and the thickness calculations due to temperature variations in the acoustic couplant medium. The steps of the present method obviate having to rely on a predetermined value for the speed of sound. The received signals can be used in either a time-domain or frequency-domain analysis, utilizing equations specific to the respective domains to determine speed of sound (time-domain), phase and group velocities (frequency-domain) and wall thickness quantities. Preferably, the workpiece is disposed in the transmission path such that during the step of transmitting the waves, they impinge substantially orthogonal to the outer and inner surfaces of the workpiece, helping to minimize distortion errors.

According to another aspect of the invention, a system for determining the wall thickness of an object and the speed of sound within the object from a single set of measured time of flight data is disclosed. The system comprises an acoustic couplant medium configured to selectively receive a tubular workpiece therein such that the workpiece, when present, is disposed within a transmission path defined in the medium. Each interface between a surface of the workpiece and the medium defines an acoustic discontinuity. The system further includes a plurality of ultrasonic wave transducers, each configured to transmit and receive signals corresponding to time of flight data from transmitted and reflected waves, as well as signal processing apparatus operatively coupled to the transducers. The signal processing apparatus is configured to calculate the speed of sound within the workpiece based on the received signals without having to determine the temperature of the workpiece. From there, it can use the time of flight data and the calculated speed of sound to calculate the thickness of each wall of the workpiece. Optionally, the signal processing apparatus is configured to effect either a time-domain or frequency-domain analysis based on time of arrival delays of at least a portion of the ultrasonic waves.

According to yet another aspect of the invention, a method of determining the wall thickness of and speed of sound within a tubular workpiece is disclosed. Steps used in the method include configuring an acoustic couplant medium, transmitting and receiving an ultrasonic wave through the medium without the tubular workpiece present in the medium, and measuring a time of flight for the transmitted wave. Other steps include placing the workpiece in the medium, generating ultrasonic waves within the medium such that at least a portion of the waves are reflected back from at least one surface of the tubular workpiece and at least a portion of the waves are transmitted through the medium and the workpiece, detecting signals correspond to a portion of the waves reflected off the at least one surface of the tubular workpiece and a portion of the waves transmitted through the couplant medium and the tubular workpiece, measuring time of flight data for each of the detected signals, calculating a speed of sound in the workpiece based on the measured time of flight data, and calculating a thickness of the walls of the workpiece based on the measured time of flight data and the calculated speed of sound. Optionally, the method can include the additional steps of extracting the spectral content of each of the detected signals from the time of flight data, and generating output signals for a plurality of discrete frequencies within the spectral content, where the output signals are proportional to the wall thickness of at least one wall of the tubular workpiece.

According to still another aspect of the invention, a method of determining the wall thickness of and speed of sound within a hollow workpiece is disclosed. The method comprising the steps of configuring an acoustic couplant medium and defining a transmission path therein, selectively disposing the hollow workpiece in the medium such that the workpiece is in the transmission path, defining an acoustic discontinuity at each interface between a surface of the workpiece and the medium along the transmission path, transmitting a plurality of ultrasonic waves through the transmission path such that at least one of the waves being transmitted is without the presence of the workpiece in the transmission path, receiving signals corresponding to the waves reflected from at least one acoustic discontinuity and the waves that traverse the substantial entirety of the transmission path, measuring time of flight data for each of the received signals, calculating a speed of sound in the workpiece based on the measured time of flight data, and calculating a thickness of each wall of the workpiece based on the measured time of flight data and the calculated speed of sound. Optionally, the method comprises the additional steps of extracting the spectral content of each of the received signals, and generating output signals for a plurality of discrete frequencies within the spectral content, where the output signals are proportional to the thickness of the walls of the workpiece.

According to another aspect of the present invention, a method of determining the wall thickness of a tubular workpiece and the speed of sound within the tubular workpiece is disclosed. The steps of the method include configuring an acoustic couplant medium, transmitting a first ultrasonic pulse through the medium when the tubular workpiece is disposed therein such that at least a portion of the first ultrasonic pulse echoes off at least one surface of the workpiece, transmitting a second ultrasonic pulse through the medium when the workpiece is disposed therein such that at least a portion of the second ultrasonic pulse echoes off at least one surface of the workpiece, transmitting a third ultrasonic pulse through the medium when the tubular workpiece is disposed therein such that at least a portion of the third ultrasonic pulse passes diametrically through the substantial entirety of both the workpiece and the medium, transmitting a fourth ultrasonic pulse through the medium when the workpiece is not disposed therein such that at least a portion of the fourth ultrasonic pulse passes diametrically through the substantial entirety of the medium, detecting signals corresponding to the transmitted first through fourth ultrasonic pulses, measuring time of flight data for the detected signals, calculating a speed of sound in the workpiece based on the measured time of flight data, and calculating a thickness of each wall of the workpiece based on the measured time of flight data and the calculated speed of sound. Optionally, the method includes the step of wherein the first ultrasonic pulse is generated by a first transmitting device, and the second ultrasonic pulse is generated by a second transmitting device.

According to yet another aspect of the present invention, a method of determining the wall thickness of a tube and speed of sound within the tube is disclosed. The method includes the steps of selectively disposing the tube in an acoustic couplant medium; defining a transmission path in the medium, defining, an acoustic discontinuity along the transmission path at each interface between a surface of the tube and the medium, generating a plurality of ultrasonic waves at least one of which is done so without the presence of the tube in the transmission path, measuring the time of flight of the portion of the waves that reflects off the first of the acoustic discontinuities encountered along the transmission path, measuring the time of flight of the portion of the waves that reflects off the second of the acoustic discontinuities encountered along the transmission path, measuring the time of flight of the portion of the waves that reflects off the third of the acoustic discontinuities encountered along the transmission path, measuring the time of flight of the portion of the waves that reflects off the fourth of the acoustic discontinuities encountered along the transmission path, measuring the time of flight of the portion of the waves that passes through the tubular member and across the substantial entirety of the transmission path, measuring the time of flight of the portion of the waves that passes across the substantial entirety of the transmission path when the tubular member is not disposed therein, calculating a speed of sound in the tube based on the measured time of flight data, and calculating a thickness of each wall of the tube based on the calculated speed of sound and the measured time of flight data.

Other objects of the present invention will be apparent in light of the description of the invention embodied herein.

BRIEF DESCRIPTION OF THE SEVERAL VIEWS OF THE DRAWINGS

The following detailed description of the preferred embodiments of the present invention can be best understood when read in conjunction with the following drawings, where like structure is indicated with like reference numerals and in which.

DETAILED DESCRIPTION OF THE PREFERRED EMBODIMENTS

Figure 1A:
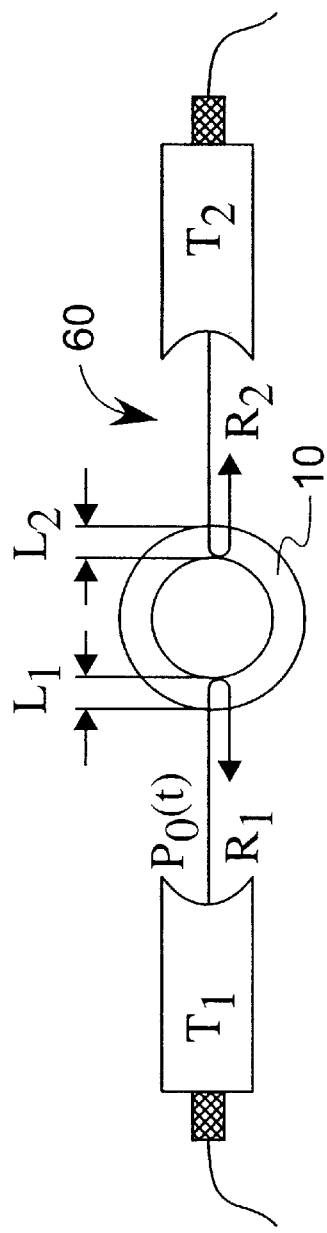
FIG. 1(a) shows the echo signal paths between each transducer and a tubular workpiece according to an embodiment of the present invention.
Figure 1B:
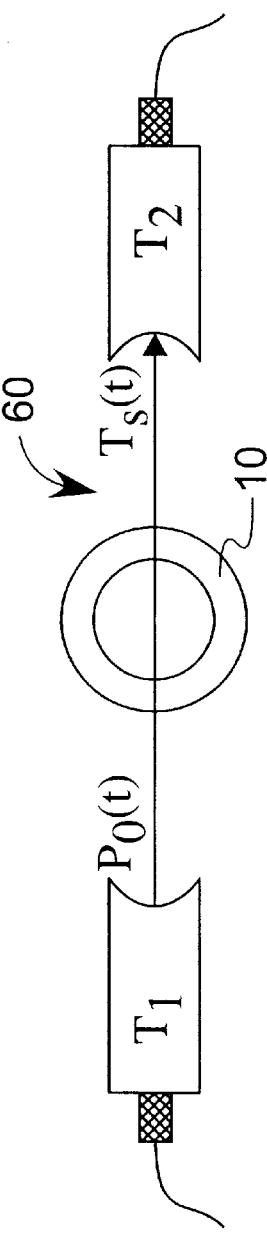
FIG. 1(b) shows the transmission signal path between transducers when the tubular workpiece is present in the signal path.
Figure 1C:
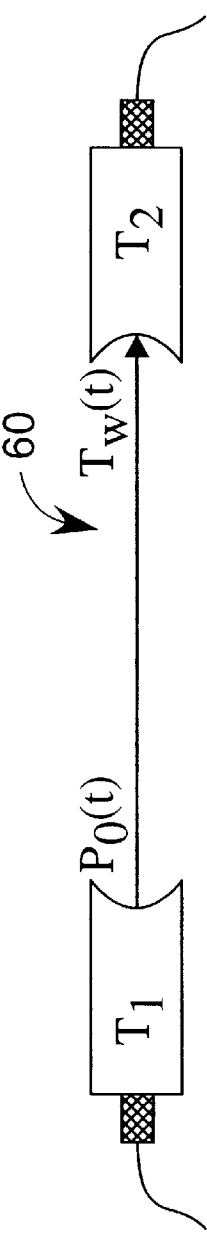
FIG. 1(c) shows the transmission signal path between transducers when the tubular workpiece is removed from the signal path.
Figure 2:
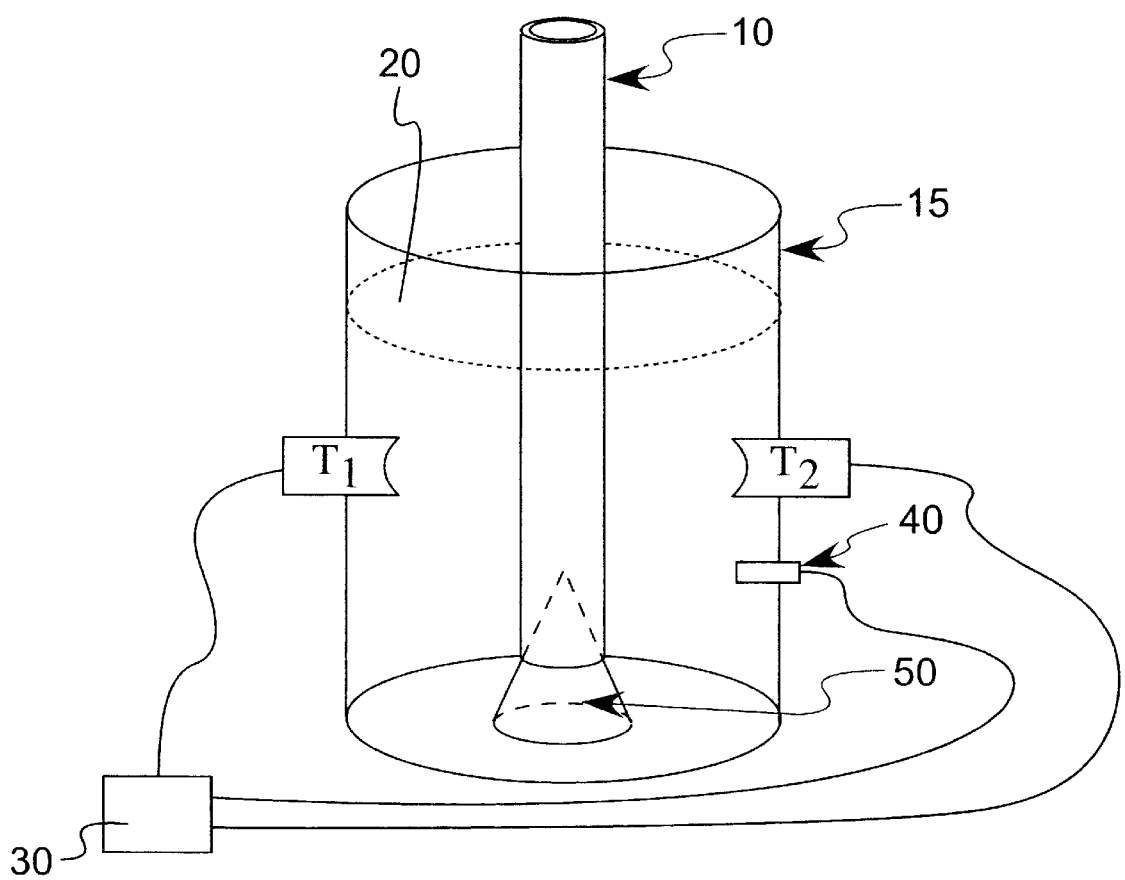
FIG. 2 shows a perspective view of the embodiment depicted in FIGS. 1(a)–(c) mounted into a measurement chamber.

Referring first to FIGS. 1A–C, 2 and 5, a set-up for the use of ultrasonic measurement of a tube is shown. In the present context, the term "measurement" and its variants is understood to include ways of sensing or otherwise detecting a particular quantity, such as time of flight data. In such a context, a measurement is a subset of the larger "determining", wherein quantities are not only measured, but processed or manipulated (such as by calculation or related computation) to produce a human- or machine-useable output. For example, measured time of flight data may be used to calculate, and thereby determine, speed of sound and thickness values. Referring with particularity to FIG. 2, the set-up includes an object to be measured 10 (in this case, a tube), a measurement chamber 15 (such as a vat), an acoustic couplant medium 20 (typically distilled water), measurement and control electronics 30, a temperature sensor 40, an object positioning device 50, and a pair of transducers T1 and T2. The transducers are capable of both sending and receiving ultrasonic pulse signals, and the path between them makes up transmission path 60. In addition, phase and echo waveform distortion due to the curvature in the tube walls can be minimized through the use of focused transducers such that the closest point on the surface of the tube being measured is placed at the transducer's focal distance. Preferably, these focused transducers are used so that the ultrasound beam width at the measurement site is three to five times smaller than the inner diameter of the tube. The control electronics 30 has numerous components, preferably including a pulser/receiver set 32, made up of a pulser 32A and receiver 32B, digitizer 34, controller and processor 35 and output 36 (typically in the form of a display, printout or data recorded to a mass storage device). A multiplexer 31 is used to switch the signals exchanged between the control electronics 30 and the transducers T1 and T2. An alternative embodiment (not shown) could use a pair of pulser/receiver sets, each dedicated to a respective transducer, thereby eliminating the need for the multiplexer 31. Alternatively, instead of using a digitizer, an analog processor (such as a comparitor and a counter, neither of which are shown) can be used to measure the time delay of received ultrasound pulses.

FIGS. 1A–C show the signal paths coming from and returning to the transducers for the dispersion measurement. In FIG. 1A, $P_0(t)$ is the initial pulse launched by the transducer T1. The echoes reflected back from the outer and inner surfaces of the first wall of the tube 10 (with a thickness $L_1$) are recorded as $R_1(t)$. Similarly, transducer T2 sends a pulse and the echoes reflected back from the two surfaces of the second wall on the opposite side (with a thickness $L_2$) are recorded as $R_2(t)$. Next, transducer T1 sends a pulse which passes through both walls of tube 10 and is recorded by T2 as $T_t(t)$, as shown by FIG. 1B. Finally, as shown in FIG. 1C, the tube 10 is removed and a pulse which passes through the transmission path 60 is recorded as $T_w(t)$. It will be appreciated by those skilled in the art that the precise order of the foregoing measurements is not critical, and that the above-recited order is meant to be representative of all such sequences. By virtue of the time of flight data acquired by the present method, one-sided transducer access to each wall of the tube is possible. This is important in applications requiring wall thickness measurement in physically small spaces, into which conventional transducers and microphones are unable to fit.

Figure 3:
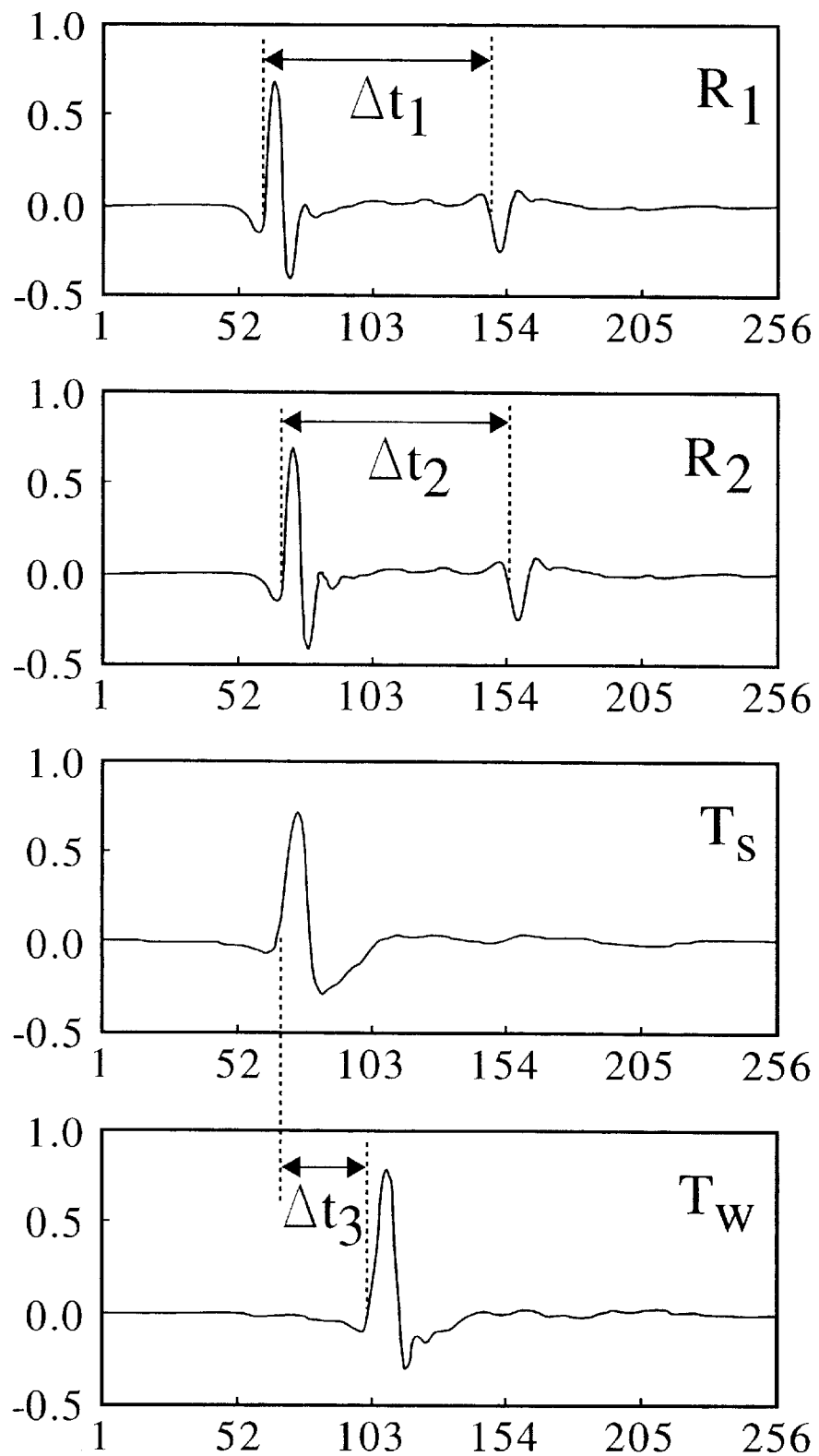
FIG. 3 shows the waveforms of recorded pulses, including pulses reflected back from the front and back surfaces of the polyethylene tube, as well as the transmitted pulses with and without the tube inserted between the two transducers, respectively.

Based on the four sets of measurements $R_1(t)$, $R_2(t)$, $T_t(t)$ and $T_w(t)$, the sound speed within and wall thickness of the tube 10 can be determined using the time-domain analysis. Referring now to FIG. 3, if $\Delta t_1$, $\Delta t_2$ and $\Delta t_3$ denote the time delay between the two echoes associated with $L_1$, the time delay between the two echoes associated with $L_2$, and the time delay between $T_t(t)$ and $T_w(t)$, respectively, the following set of equations can be used:

$$\Delta t_1 = \frac{2L_1}{c} \tag{1}$$

$$\Delta t_2 = \frac{2L_2}{c} \tag{2}$$

$$\Delta t_3 = \frac{L_1 + L_2}{c_w(T)} - \frac{L_1 + L_2}{c} \tag{3}$$

where $c_w(T)$ is the temperature-dependent speed of sound in water. From the above three equations, c can first be solved:

$$c = c_w(T)\left[\frac{2\Delta t_3}{\Delta t_1 + \Delta t_2} + 1\right] \tag{4}$$

From equation (4), it can be seen that the value of c, the speed of sound in the object being measured, is only dependent on the speed of sound in the water (which can be easily determined from the measured temperature) and the three time delays $\Delta t_1$, $\Delta t_2$ and $\Delta t_3$ associated with the various times of flight. This is significant, as errors associated with temperature differences between the water and the object being measured are reduced, since any temperature dependencies of the speed of sound fall out of the time of flight data and subsequent calculations. Using the value of c obtained by equation (4), the thickness of the two walls $L_1$ and $L_2$ can then be solved as:

$$L_1 = \frac{c\Delta t_1}{2} \tag{5}$$

$$L_2 = \frac{c\Delta t_2}{2} \tag{6}$$

In situations where a dispersive tube material is used, additional accuracy in the determination of c, $L_1$ and $L_2$ can be determined based on the phase differences of the pulses using the frequency domain analysis. By using $A(f)e^{-j\theta(f)}$ to represent the Fourier transform of the pulses, the phase velocity $V_p(f)$ of the tube can be obtained from the phase spectra of the two transmitted pulses:

$$\frac{1}{V_p(f)} = \frac{\Delta \theta_1(f)}{4\pi f L_1} \tag{7}$$

$$\frac{1}{V_p(f)} = \frac{\Delta \theta_2(f)}{4\pi f L_2} \tag{8}$$

$$\frac{1}{V_p(f)} = -\frac{\Delta \theta_3(f)}{2\pi f(L_1 + L_2)} + \frac{1}{c_w(T)} \tag{9}$$

where $\Delta\theta_1(f)$ and $\Delta\theta_2(f)$ are, respectively, the differences between the phase spectra of the two echoes associated with $L_1$ and the two echoes associated with $L_2$, after the extra 180° phase shift of the second echo is removed, and $\Delta\theta_3(f)$ is the difference between the phase spectra of the two transmitted pulses $T_w(t)$ and $T_t(t)$. It will be appreciated by those skilled in the art that equations (7) through (9) are the frequency-domain analogues to time-domain equations (1) through (3). In the preceding derivation, it was assumed that for all practical purposes the dispersion of water is negligible. From these three equations, $V_p(f)$, $L_1$ and $L_2$ can be solved:

$$V_p(f) = c_w(T)\left[\frac{2\Delta\theta_3(f)}{\Delta\theta_1(f) + \Delta\theta_2(f)} + 1\right] \tag{10}$$

$$L_1 = \frac{\Delta\theta_1}{4\pi f} V_p(f) \tag{11}$$

$$L_2 = \frac{\Delta\theta_2}{4\pi f} V_p(f) \tag{12}$$

Equation (10) for $V_p(f)$ gives the phase velocity as a function of frequency. As with equation (4) of the time-domain analysis, it highlights that the present method does not require direct measurement of the temperature of the tube walls. From $V_p(f)$, the group velocity, $V_g(f)$, can be calculated:

$$V_g(f) = \frac{V_p(f)}{1 - \frac{f}{V_p(f)} \frac{dV_p(f)}{df}} \tag{13}$$

If the medium is dispersionless (such that $V_p$ is a constant), then the phase velocity $V_p$, group velocity $V_g$, and the speed of sound c, defined in the previous time-domain analysis, are all the same. On the other hand, if the dispersion is not negligible, $V_g$ can be significantly different from $V_p$, and c takes a value of $V_g$ at some frequency near the center frequency of the transducer T1.

The following experimental example will be used to explain the attributes of the present invention. In the experiment, a polyethylene tube sample is used which has a nominal outer diameter of 9.53 mm (⅜ inches) and a nominal inner diameter of 6.35 mm (¼ inches). Both time-domain analysis and frequency-domain analysis are performed. Additional experimental results for four tube samples made from different materials can be found in an article entitled *Simultaneous Measurement of Sound Velocity and Wall Thickness of a Tube,* Ultrasonics 39 (2001) 407–411, by the present inventor, and hereby incorporated by reference.

The experimental setup is shown conceptually in FIGS. 1A–C, 2, and 5. A pair of identical transducers (Panametrics V309, 5.0 MHz, 13-mm aperture, point focus, 25.4-mm focal distance) are used as T1 and T2. The outer surface of the tube 10 is placed near the focal distance of the transducers. Switching can be accomplished either manually or through a conventional multiplexer 31, while the pulser/receiver set 32 is a Panametrics 5052PR. The amplified pulse is digitized by a SONY/TEK 390AD programmable digitizer 34, which includes an adjustable digital delay for triggering the sampling window. Each sampling window contains 256 samples, and has a sampling frequency of 60 MHz. The signals are averaged 30 times and then transferred to the controller and processor 35 (such as that found in a conventional personal computer) and processed using a standard mathematics software package, such as MATLAB, distributed by MathWorks, Natick, Mass. Output 36 can be in the form of printouts, visual display or data sent to a mass storage device (such as a hard disk drive). The water temperature was measured by probe 40, and found to be 21° C., which corresponds to a $c_w(T)$ of 1485 m/s.

Referring again to FIG. 3, the waveforms of the two reflected signals $R_1(t)$, $R_2(t)$ and the two transmitted signals $T_s(t)$, $T_w(t)$ are shown. For the time-domain analysis, the time delays $\Delta t_1$ and $\Delta t_2$ are measured from the zero-crossing right before the largest positive peak of the first echo to the zero-crossing right before the largest negative peak of the second echo to take account for the extra 180° phase shift between the two echoes. The time delay $\Delta t_3$ is measured from the zero-crossing right before the largest positive peak of $T_s$ to the zero-crossing right before the largest positive peak of $T_w$. From the measured time delays, c, $L_1$ and $L_2$ are calculated using equations (4), (5) and (6). The results are summarized on the left side of Table 1.

TABLE 1

Results from the polyethylene tube using the time-domain analysis and frequency-domain analysis.

| Time-domain Analysis | Frequency-domain Analysis | |
|---|---|---|
| $\Delta t_1$ = 1.418 (μs) | $V_P$ = 2067 + 2.156 f(m/s) | [f = 2~8 MHz] |
| $\Delta t_2$ = 1.415 (μs) | $V_g$ = 2089 (m/s) | [f = 5 MHz] |
| $\Delta t_3$ = 0.597 (μs) | | |
| c = 2.11 × 10³ (m/s) | | |
| $L_1$ = 1.50 (mm) | $L_1$ = 1.483 ± 0.005 (mm) | [f = 3~7 MHz] |
| $L_2$ = 1.49 (mm) | $L_2$ = 1.484 ± 0.004 (mm) | [f = 3~7 MHz] |

Figure 4:
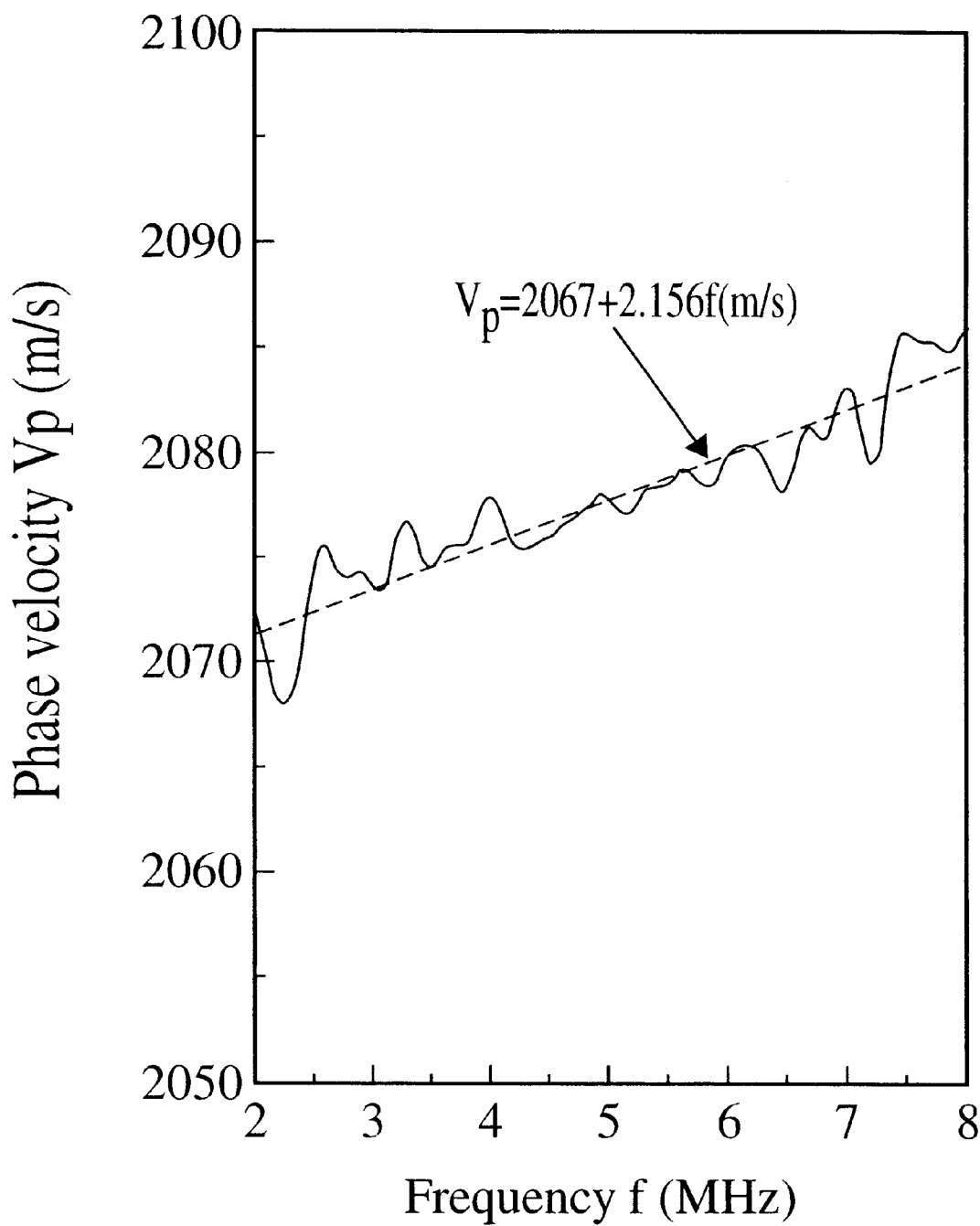
FIG. 4 shows a plot of dispersion for data taken from measurements on a polyethylene tube.

To perform the frequency-domain analysis, the two echoes contained in $R_1(t)$ are first separated while keeping their temporal relation. The phase difference $\Delta\theta_1$ between the two echoes is then determined using a procedure described in an article entitled *Measurement of Acoustic Dispersion Using Both Transmitted and Reflected Pulses,* J. Acoust. Soc. Am. 107 (2000) 801, (hereinafter Measurement Article) by the present inventor, and hereby incorporated by reference. The phase difference $\Delta\theta_2$ between the two echoes contained in $R_2(t)$, as well as the phase difference $\Delta\theta_3$ between $T_w(t)$ and $T_s(t)$, is also determined in a similar way. The phase velocity $V_p(f)$ is then calculated using equation (10). Referring now to FIG. 4, the solid line represents $V_p(f)$, calculated from data taken and manipulated according to equation (10), in the frequency range between 2 and 8 MHz. A linear regression (dashed) line having a slope of 2.156 m/s per MHz is also shown. Using this value of the slope and a phase velocity of 2078 m/s at 5MHz, the group velocity at 5 MHz is calculated using equation (13) as 2089 m/s. This value is 1% smaller than 2110 m/s value determined using the time-domain analysis. When equations (11) and (12) are used to calculate the wall thickness, the values of $L_1$ and $L_2$ are actually functions of frequency; however, the changes of $L_1$ and $L_2$ within the useful frequency range of the measurement system, which are due to noise, should be very small. The means and standard deviations of $L_1$ and $L_2$ in the frequency range of 3 to 7 MHz are listed in Table 1. As with the velocity calculations, the difference between the thickness determined by the time-domain analysis and the frequency-domain analysis is about 1%. The general trend shown in FIG. 4, that of the phase velocity $V_p$ increasing with increasing frequency, is typical of most materials, and is consistent with predictions. The close agreement between the time-domain value for the speed of sound and the frequency-domain value for the phase velocity also indicates that the present method is internally consistent, and that the polyethylene used in the tube does not exhibit marked dispersive properties.

Figure 5:
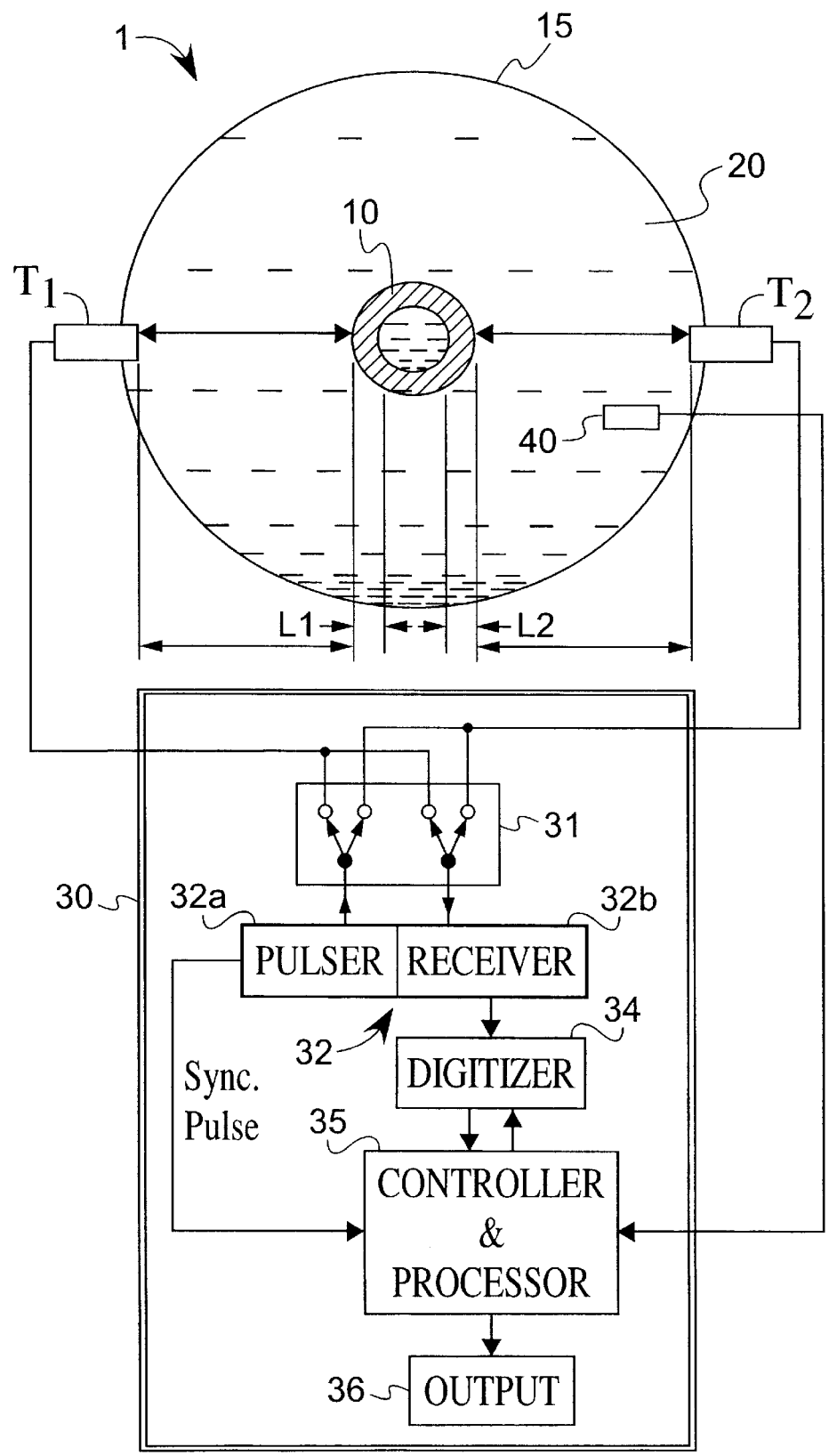
FIG. 5 shows a block diagram representative of the system of the present invention for measuring the wall thickness of a tubular object.

When the curve of $V_p$ in FIG. 4 for the tube is compared with the smooth curves for measurements made on flat plates, as shown in FIGS. 5 through 7 of the aforementioned Measurement Article, it is apparent that the phase velocity obtained from the tube sample is significantly noisier. This is to be expected, as phase distortion is produced by the curved tube walls, since portions of the wave pass through longer, refracted paths than others. The pulse returns emanating from the curved wall surface make precise determination of the onset of pulse detection more difficult, as there is a less clear line of demarcation between discrete pulses. This distortion is decreased when the ratio of the beam width to the diameter of the tube decreases. For example, focused transducers should be used and the front surface of the tube should be placed at the focal distance of the transducer. In the experiment with the polyethylene tube, the −6 dB beam width is about 0.6 mm, which is ten times smaller than the inner diameter of the tube. Based on this, a general guideline is that the beam width at the measurement site should be at least between three and five times smaller than the inner diameter of the tube. Even with the rippling effect caused by distortion, the size of the individual excursions are small (on the order of 3 m/s or less) relative to the phase velocity spread (between 10 and 15 m/s) over the frequency band between 2 and 8 MHz. The rippling effect shown in FIG. 4 highlights two important observations: first, that the speed of an acoustic disturbance passing through a material (in this case, a common tube material such as polyethylene) varies with frequency, and second, that by using a focused transducer, even more accurate measurement is possible, as the effects of noise are better appreciated, and noise-lessening measures may be undertaken. Regarding this second point, it will be appreciated by those skilled in the art that the noise shown in FIG. 4 is not unique to the present invention; conventional measurements taken in the time-domain on tubular objects also capture the noise, it is just that such noise does not show up on a plot such as FIG. 4. The conventional approach can be fraught with measurement inaccuracy for the very reason that because the noise does not manifest itself in the plotted or tabulated results, it is assumed to not exist. By contrast, the measurement approach of the present invention allows the user to determine if modifications to the hardware setup or calculation routine is necessary to ensure optimum accuracy.

Having described the invention in detail and by reference to preferred embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method of determining the wall thickness of a tubular workpiece and the speed of sound within said tubular workpiece from a single set of measured time of flight data, said method comprising the steps of:
    configuring an acoustic couplant medium;
    defining a transmission path in said acoustic couplant medium;
    selectively disposing said tubular workpiece in said acoustic couplant medium such that said tubular workpiece is in said transmission path;
    defining, along said transmission path, an acoustic discontinuity at each interface between a surface of said tubular workpiece and said acoustic couplant medium;
    transmitting a plurality of ultrasonic waves through said transmission path, at least one of said plurality of ultrasonic waves being transmitted without the presence of said tubular workpiece in said transmission path;
    receiving signals corresponding to:
        said plurality of transmitted ultrasonic waves that are reflected from at least one of said acoustic discontinuities; and
        said plurality of transmitted ultrasonic waves that traverse the substantial entirety of said transmission path;
    measuring time of flight data for each of said received signals;
    calculating a speed of sound in said tubular workpiece based on said measured time of flight data; and
    calculating a thickness of each wall of said tubular workpiece based on said measured time of flight data and said calculated speed of sound.

2. A method according to claim 1, comprising the additional step of compensating said speed of sound and said thickness calculations due to temperature variations in said acoustic couplant medium.

3. A method according to claim 2, wherein said step of calculating a speed of sound is performed to the exclusion of a predetermined speed of sound quantity in said tubular workpiece.

4. A method according to claim 1, wherein said received signals correspond to time delays of arrival of at least a portion of said ultrasonic waves, said received signals configured to effect a time-domain analysis.

5. A method according to claim 4, wherein said thickness of a first of said walls is calculated using the equation $$L_1 = \frac{c \Delta t_1}{2}$$

and said thickness of a second of said walls is calculated using the equation $$L_2 = \frac{c \Delta t_2}{2},$$

where said speed of sound c is calculated using the equation $$c = c_w(T)\left[\frac{2\Delta t_3}{\Delta t_1 + \Delta t_2} + 1\right],$$

where $c_w(T)$ represents a predetermined value for the speed of sound of said ultrasonic waves in said acoustic couplant medium as a function of temperature, and said measured time of flight data corresponds to $\Delta t_1$, $\Delta t_2$ and $\Delta t_3$, which represent time of arrival differences associated with reflections off the inner and outer surfaces of said first wall, reflections off the inner and outer surfaces of said second wall, and time of arrival differences associated with transmission of said waves through said substantial entirety of said transmission path based on said selective presence of said workpiece in said transmission path, respectively.

6. A method according to claim 1, wherein said received signals correspond to phase differences of at least a portion of said ultrasonic waves, said received signals configured to effect a frequency-domain analysis.

7. A method according to claim 6, wherein said thickness of a first of said walls is calculated using the equation $$L_1 = \frac{\Delta \theta_1}{4\pi f} V_p(f)$$

and said thickness of a second of said walls is calculated using the equation $$L_2 = \frac{\Delta \theta_2}{4\pi f} V_p(f),$$

where said speed of sound is represented by a phase velocity as a function of frequency $V_p(f)$, and is calculated using the equation $$V_p(f) = c_w(T)\left[\frac{2\Delta \theta_3(f)}{\Delta \theta_1(f) + \Delta \theta_2(f)} + 1\right],$$

where $c_w(T)$ represents a predetermined value for the speed of sound of said ultrasonic waves in said acoustic couplant medium as a function of temperature, and said measured time of flight data corresponds $\Delta \theta_1(f)$, $\Delta \theta_2(f)$ and $\Delta \theta_3(f)$, which represent phase spectra differences at each frequency associated with reflections off the inner and outer surfaces of said first wall, reflections off the inner and outer surfaces of said second wall, and phase spectra differences associated with transmission of said waves through said substantial entirety of said transmission path based on said selective presence of said workpiece in said transmission path, respectively.

8. A method according to claim 1, wherein said tubular workpiece is disposed in said transmission path such that during the step of transmitting a plurality of ultrasonic waves, said waves impinge substantially orthogonal to the outer and inner surfaces of said tubular workpiece.

9. A system for determining the wall thickness of an object and the speed of sound within said object from a single set of measured time of flight data, said system comprising:
  an acoustic couplant medium with a transmission path defined therein, said acoustic couplant medium configured to selectively receive a tubular workpiece disposed in said transmission path such that each interface between a surface of said tubular workpiece and said acoustic couplant medium defines an acoustic discontinuity;
  a plurality of ultrasonic wave transducers cooperative with said acoustic couplant medium, said plurality of ultrasonic wave transducers configured to transmit and receive signals, said received signals corresponding to time of flight data from:
    reflections of at least a portion of said ultrasonic waves from said acoustic discontinuities; and
    transmitted ultrasonic waves that traverse the substantial entirety of said transmission path;
  signal processing apparatus operatively coupled to said plurality of ultrasonic wave transducers, said signal processing apparatus configured to:
    calculate the speed of sound within said tubular workpiece based on said received signals without having to determine the temperature of said tubular workpiece; and
    calculate the thickness of each wall of said tubular workpiece based on said time of flight data and said calculated speed of sound.

10. A system according to claim 9, wherein said signal processing apparatus is configured to effect a time-domain analysis based on time delays of arrival of at least a portion of said ultrasonic waves.

11. A system according to claim 9, wherein said signal processing apparatus is configured to effect a frequency-domain analysis based on time delays of arrival of at least a portion of said ultrasonic waves.

12. A method of determining the wall thickness of and speed of sound within a tubular workpiece, said method comprising the steps of:
  configuring an acoustic couplant medium;
  transmitting an ultrasonic wave through said acoustic couplant medium;
  receiving said transmitted ultrasonic wave;
  measuring a time of flight for said transmitted ultrasonic wave;
  placing said tubular workpiece in said acoustic couplant medium;
  generating ultrasonic waves within said acoustic couplant medium such that at least a portion of said waves are reflected back from at least one surface of said tubular workpiece, and at least a portion of said waves are transmitted through said couplant medium and said tubular workpiece;
  detecting, from said waves, signals corresponding to:
    a portion reflected off said at least one surface of said tubular workpiece; and
    a portion transmitted through said couplant medium and said tubular workpiece;
  measuring time of flight data for each of said detected signals;
  calculating a speed of sound in said tubular workpiece based on said measured time of flight data; and
  calculating a thickness of each wall of said tubular workpiece based on said measured time of flight data and said calculated speed of sound.

13. A method according to claim 12, comprising the additional steps of:
  extracting the spectral content of each of said detected signals from said time of flight data; and
  generating output signals for a plurality of discrete frequencies within said spectral content, said output signals proportional to the wall thickness of at least one wall of said tubular workpiece.

14. A method of determining the wall thickness of and speed of sound within a hollow workpiece, said method comprising the steps of:
  configuring an acoustic couplant medium;
  defining a transmission path in said acoustic couplant medium;
  selectively disposing said hollow workpiece in said acoustic couplant medium such that said hollow workpiece is in said transmission path;
  defining, along said transmission path, an acoustic discontinuity at each interface between a surface of said hollow workpiece and said acoustic couplant medium;
  transmitting a plurality of ultrasonic waves through said transmission path, at least one of said plurality of ultrasonic waves being transmitted without the presence of said hollow workpiece in said transmission path;
  receiving signals corresponding to:
    said plurality of transmitted ultrasonic waves that are reflected from at least one acoustic discontinuity; and
    said plurality of transmitted ultrasonic waves that traverse the substantial entirety of said transmission path;
  measuring time of flight data for each of said received signals;
  calculating a speed of sound in said hollow workpiece based on said measured time of flight data; and
  calculating a thickness of each wall of said hollow workpiece based on said measured time of flight data and said calculated speed of sound.

15. A method according to claim 14, comprising the additional steps of:
  extracting, based on said time of flight data, the spectral content of each of said received signals; and
  generating output signals for a plurality of discrete frequencies within said spectral content, said output signals proportional to the thickness of said hollow workpiece.

16. A method of determining the wall thickness of a tubular workpiece and the speed of sound within said tubular workpiece, said method comprising the steps of:
  configuring an acoustic couplant medium;
  transmitting a first ultrasonic pulse through said acoustic couplant medium when said tubular workpiece is disposed therein such that at least a portion of said first ultrasonic pulse echoes off at least one surface of said tubular workpiece;
  transmitting a second ultrasonic pulse through said acoustic couplant medium when said tubular workpiece is disposed therein such that at least a portion of said second ultrasonic pulse echoes off at least one surface of said tubular workpiece;
  transmitting a third ultrasonic pulse through said acoustic couplant medium when said tubular workpiece is disposed therein such that at least a portion of said third ultrasonic pulse passes diametrically through the substantial entirety of both said tubular workpiece and said acoustic couplant medium;

transmitting a fourth ultrasonic pulse through said acoustic couplant medium when said tubular workpiece is not disposed therein such that at least a portion of said fourth ultrasonic pulse passes diametrically through the substantial entirety of said acoustic couplant medium;

detecting signals corresponding to said transmitted first, second, third and fourth ultrasonic pulses;

measuring time of flight data for said detected signals;

calculating a speed of sound in said tubular workpiece based on said measured time of flight data; and calculating a thickness of each wall of said tubular workpiece based on said measured time of flight data and said calculated speed of sound.

17. A method according to claim 16, wherein said first ultrasonic pulse is generated by a first transmitting device, and said second ultrasonic pulse is generated by a second transmitting device.

18. A method of determining the wall thickness of a tube and speed of sound within said tube, said method comprising the steps of:

selectively disposing said tube in an acoustic couplant medium;

defining a transmission path in said acoustic couplant medium;

defining, along said transmission path, an acoustic discontinuity at each interface between a surface of said tube and said acoustic couplant medium;

generating a plurality of ultrasonic waves at least one of which is generated without the presence of said tube in said transmission path;

measuring the time of flight of the portion of said plurality of ultrasonic waves that reflects off the first of said acoustic discontinuities encountered along said transmission path;

measuring the time of flight of the portion of said plurality of ultrasonic waves that reflects off the second of said acoustic discontinuities encountered along said transmission path;

measuring the time of flight of the portion of said plurality of ultrasonic waves that reflects off the third of said acoustic discontinuities encountered along said transmission path;

measuring the time of flight of the portion of said plurality of ultrasonic waves that reflects off the fourth of said acoustic discontinuities encountered along said transmission path;

measuring the time of flight of the portion of said plurality of ultrasonic waves that passes through said tubular member and across the substantial entirety of said transmission path;

measuring the time of flight of the portion of said plurality of ultrasonic waves that passes across the substantial entirety of said transmission path when said tubular member is not disposed therein;

calculating a speed of sound in said tube based on said measured time of flight data; and calculating a thickness of each wall of said tube based on said calculated speed of sound and said measured time of flight data.

* * * * *